United States Patent
St. George-Hyslop et al.

(10) Patent No.: US 6,783,982 B1
(45) Date of Patent: Aug. 31, 2004

(54) PROTEINS RELATED TO NEURONAL REGENERATION AND USES THEREOF

(75) Inventors: Peter H. St. George-Hyslop, Toronto (CA); Paul E. Fraser, Toronto (CA)

(73) Assignee: The Governing Council of The University of Toronto, Toronto (CA)

(*) Notice: Subject to any disclaimer, the term of this patent is extended or adjusted under 35 U.S.C. 154(b) by 0 days.

(21) Appl. No.: 09/501,171

(22) Filed: Feb. 9, 2000

Related U.S. Application Data

(60) Provisional application No. 60/119,835, filed on Feb. 12, 1999.

(51) Int. Cl.[7] .......................... C12N 5/08; C07K 17/00; A61K 38/00
(52) U.S. Cl. .......................... 435/368; 530/350; 514/2
(58) Field of Search .......................... 435/368; 530/350, 530/300; 514/2–12

(56) References Cited

U.S. PATENT DOCUMENTS

| | | | | |
|---|---|---|---|---|
| 5,475,088 A | * | 12/1995 | Perez-Polo | 530/326 |
| 5,840,540 A | | 11/1998 | St. George-Hyslop et al. | 435/69.1 |
| 5,986,054 A | | 11/1999 | St. George-Hyslop et al. | 530/350 |
| 6,020,143 A | | 2/2000 | St. George-Hyslop et al. | 435/7.1 |

FOREIGN PATENT DOCUMENTS

| WO | WO 96/34099 | 10/1996 |
|---|---|---|
| WO | WO 97/27296 | 7/1997 |
| WO | WO 98/25142 | 6/1998 |

OTHER PUBLICATIONS

Tanahasi et al., Neuroreport, 10:563–568, Feb. 25, 1999.*
Liuzzi et al., Neurosurg. Clinics of N. Am., 2(1):31–42, Jan. 1991.*
Jackowski et al., Br. J. of Neurosurg. 9:303–317, 1995.*
Skolnick et al., Trends in Biotech., 18(1):34–39, 2000.*
McDonald et al., Annals of the Rheumatic Diseases, 47(3):232–40, 1988.*
Tanake–Matakatsu et al., 122(12):3697–705, 1996.*
Stamatoglou et al., Exp. Cell Res., 198(1):179–82, 1992.*
Daniloff, Joanne K. et al., "Altered Expression of Neuronal Cell Adhesion Molecules Induced by Nerve Injury and Repair," The Journal of Cell Biology, p. 929–945 (Sep. 1986).
Gibson, Karen L. et al., "Peripheral Nerve Repair," The Compendium, p. 938–945 (Aug. 1989).
Walker, Michael D., "Acute Spinal–Cord Injury," The New England Journal of Medicine, p. 1885–1887 (Jun. 27, 1991).
Lee, Michael K. et al., "Expression of Presenilin 1 and 2 (PS1 and PS2) in Human and Murine Tissues," The Journal of Neuroscience, p. 7513–7525 (Dec. 1, 1996).
Paffenholz, Rainer et al., "Identification and Localization of a Neurality Expressed Member of the Plakoglobin/Armadillo Multigene Family," Differentiation, p. 293–304 (1997).
Loureiro, Joseph et al., "Roles of Armadillo, a Drosophila Catenin, During Central Nervous System Development," Current Biology, p. 622–632 (May 6, 1998).
White, Phoebe et al., "Signaling and Adhesion Activities of Mammalian β–Catenin and Plakoglobin in Drosophila," The Journal of Cell Biology, p. 183–195 (Jan. 12, 1998).
Kawamura, Yuuki et al., "Expression of the mRNA for Two Isoforms of Neural Plakophilin–Related Arm Repeat Protein/δ–Catenin in Rodent Neurons and Glial Cells," Neuroscience Letters, p. 185–188 (1999).

* cited by examiner

*Primary Examiner*—Gary Kunz
*Assistant Examiner*—Sharon Turner
(74) *Attorney, Agent, or Firm*—Darby & Darby

(57) ABSTRACT

The invention provides a method for stimulating nerve growth, which also includes nerve regeneration, by contacting nerve cells with human Neural Plakophilin Related Armadillo Protein (hNPRAP). In a specific embodiment, hNPRAP causes the development of numerous long, cellular extensions, which are similar to axonal sprouting observed during neuronal regeneration and synapse formation. The invention further relates to pharmaceutical compositions comprising an hNPRAP, or alternatively a gene therapy vector that expresses an hNPRAP. Also provided are methods for identifying substances that modulate expression of hNPRAP.

2 Claims, No Drawings

SEQUENCE LISTING

<160> NUMBER OF SEQ ID NOS: 6

<210> SEQ ID NO 1
<211> LENGTH: 467
<212> TYPE: PRT
<213> ORGANISM: human

<400> SEQUENCE: 1

```
Met Thr Glu Leu Pro Ala Pro Leu Ser Tyr Phe Gln Asn Ala Gln Met
1               5                   10                  15

Ser Glu Asp Asn His Leu Ser Asn Thr Val Arg Ser Gln Asn Asp Asn
            20                  25                  30

Arg Glu Arg Gln Glu His Asn Asp Arg Arg Ser Leu Gly His Pro Glu
        35                  40                  45

Pro Leu Ser Asn Gly Arg Pro Gln Gly Asn Ser Arg Gln Val Val Glu
    50                  55                  60

Gln Asp Glu Glu Glu Asp Glu Glu Leu Thr Leu Lys Tyr Gly Ala Lys
65                  70                  75                  80

His Val Ile Met Leu Phe Val Pro Val Thr Leu Cys Met Val Val Val
                85                  90                  95

Val Ala Thr Ile Lys Ser Val Ser Phe Tyr Thr Arg Lys Asp Gly Gln
            100                 105                 110

Leu Ile Tyr Thr Pro Phe Thr Glu Asp Thr Glu Thr Val Gly Gln Arg
        115                 120                 125

Ala Leu His Ser Ile Leu Asn Ala Ala Ile Met Ile Ser Val Ile Val
    130                 135                 140

Val Met Thr Ile Leu Leu Val Val Leu Tyr Lys Tyr Arg Cys Tyr Lys
145                 150                 155                 160

Val Ile His Ala Trp Leu Ile Ile Ser Ser Leu Leu Leu Leu Phe Phe
                165                 170                 175
```

-continued

```
Phe Ser Phe Ile Tyr Leu Gly Glu Val Phe Lys Thr Tyr Asn Val Ala
            180                 185                 190
Val Asp Tyr Ile Thr Val Ala Leu Leu Ile Trp Asn Phe Gly Val Val
        195                 200                 205
Gly Met Ile Ser Ile His Trp Lys Gly Pro Leu Arg Leu Gln Gln Ala
    210                 215                 220
Tyr Leu Ile Met Ile Ser Ala Leu Met Ala Leu Val Phe Ile Lys Tyr
225                 230                 235                 240
Leu Pro Glu Trp Thr Ala Trp Leu Ile Leu Ala Val Ile Ser Val Tyr
                245                 250                 255
Asp Leu Val Ala Val Leu Cys Pro Lys Gly Pro Leu Arg Met Leu Val
            260                 265                 270
Glu Thr Ala Gln Glu Arg Asn Glu Thr Leu Phe Pro Ala Leu Ile Tyr
        275                 280                 285
Ser Ser Thr Met Val Trp Leu Val Asn Met Ala Glu Gly Asp Pro Glu
    290                 295                 300
Ala Gln Arg Arg Val Ser Lys Asn Ser Lys Tyr Asn Ala Glu Ser Thr
305                 310                 315                 320
Glu Arg Glu Ser Gln Asp Thr Val Ala Glu Asn Asp Asp Gly Gly Phe
                325                 330                 335
Ser Glu Glu Trp Glu Ala Gln Arg Asp Ser His Leu Gly Pro His Arg
            340                 345                 350
Ser Thr Pro Glu Ser Arg Ala Ala Val Gln Glu Leu Ser Ser Ser Ile
        355                 360                 365
Leu Ala Gly Glu Asp Pro Glu Glu Arg Gly Val Lys Leu Gly Leu Gly
    370                 375                 380
Asp Phe Ile Phe Tyr Ser Val Leu Val Gly Lys Ala Ser Ala Thr Ala
385                 390                 395                 400
Ser Gly Asp Trp Asn Thr Thr Ile Ala Cys Phe Val Ala Ile Leu Ile
                405                 410                 415
Gly Leu Cys Leu Thr Leu Leu Leu Ala Ile Phe Lys Lys Ala Leu
            420                 425                 430
Pro Ala Leu Pro Ile Ser Ile Thr Phe Gly Leu Val Phe Tyr Phe Ala
        435                 440                 445
Thr Asp Tyr Leu Val Gln Pro Phe Met Asp Gln Leu Ala Phe His Gln
    450                 455                 460
Phe Tyr Ile
465

<210> SEQ ID NO 2
<211> LENGTH: 448
<212> TYPE: PRT
<213> ORGANISM: human

<400> SEQUENCE: 2

Met Leu Thr Phe Met Ala Ser Asp Ser Glu Glu Val Cys Asp Glu
1               5                   10                  15
Arg Thr Ser Leu Met Ser Ala Glu Ser Pro Thr Pro Arg Ser Cys Gln
                20                  25                  30
Glu Gly Arg Gln Gly Pro Glu Asp Gly Glu Asn Thr Ala Gln Trp Arg
            35                  40                  45
Ser Gln Glu Asn Glu Glu Asp Gly Glu Glu Asp Pro Asp Arg Tyr Val
        50                  55                  60
Cys Ser Gly Val Pro Gly Arg Pro Pro Gly Leu Glu Glu Glu Leu Thr
```

-continued

```
             65                  70                  75                  80
Leu Lys Tyr Gly Ala Lys His Val Ile Met Leu Phe Val Pro Val Thr
                    85                  90                  95
Leu Cys Met Ile Val Val Ala Thr Ile Lys Ser Val Arg Phe Tyr
                100                 105                 110
Thr Glu Lys Asn Gly Gln Leu Ile Tyr Thr Pro Phe Thr Glu Asp Thr
                115                 120                 125
Pro Ser Val Gly Gln Arg Leu Leu Asn Ser Val Leu Asn Thr Leu Ile
            130                 135                 140
Met Ile Ser Val Ile Val Val Met Thr Ile Phe Leu Val Val Leu Tyr
145                 150                 155                 160
Lys Tyr Arg Cys Tyr Lys Phe Ile His Gly Trp Leu Ile Met Ser Ser
                165                 170                 175
Leu Met Leu Leu Phe Leu Phe Thr Tyr Ile Tyr Leu Gly Glu Val Leu
                180                 185                 190
Lys Thr Tyr Asn Val Ala Met Asp Tyr Pro Thr Leu Leu Leu Thr Val
                195                 200                 205
Trp Asn Phe Gly Ala Val Gly Met Val Cys Ile His Trp Lys Gly Pro
210                 215                 220
Leu Val Leu Gln Gln Ala Tyr Leu Ile Met Ile Ser Ala Leu Met Ala
225                 230                 235                 240
Leu Val Phe Ile Lys Tyr Leu Pro Glu Trp Ser Ala Trp Val Ile Leu
                245                 250                 255
Gly Ala Ile Ser Val Tyr Asp Leu Val Ala Val Leu Cys Pro Lys Gly
                260                 265                 270
Pro Leu Arg Met Leu Val Glu Thr Ala Gln Glu Arg Asn Glu Pro Ile
                275                 280                 285
Phe Pro Ala Leu Ile Tyr Ser Ser Ala Met Val Trp Thr Val Gly Met
            290                 295                 300
Ala Lys Leu Asp Pro Ser Ser Gln Gly Ala Leu Gln Leu Pro Tyr Asp
305                 310                 315                 320
Pro Glu Met Glu Glu Asp Ser Tyr Asp Ser Phe Gly Glu Pro Ser Tyr
                325                 330                 335
Pro Glu Val Phe Glu Pro Pro Leu Thr Gly Tyr Pro Gly Glu Glu Leu
                340                 345                 350
Glu Glu Glu Glu Glu Arg Gly Val Lys Leu Gly Leu Gly Asp Phe Ile
                355                 360                 365
Phe Tyr Ser Val Leu Val Gly Lys Ala Ala Ala Thr Gly Ser Gly Asp
            370                 375                 380
Trp Asn Thr Thr Leu Ala Cys Phe Val Ala Ile Leu Ile Gly Leu Cys
385                 390                 395                 400
Leu Thr Leu Leu Leu Leu Ala Val Phe Lys Lys Ala Leu Pro Ala Leu
                405                 410                 415
Pro Ile Ser Ile Thr Phe Gly Leu Ile Phe Tyr Phe Ser Thr Asp Asn
                420                 425                 430
Leu Val Arg Pro Phe Met Asp Thr Leu Ala Ser His Gln Leu Tyr Ile
                435                 440                 445
```

<210> SEQ ID NO 3
<211> LENGTH: 4746
<212> TYPE: DNA
<213> ORGANISM: human

<400> SEQUENCE: 3

-continued

```
gccagcatcc cttgtcccgc ggccggctca gacaacaaaa gcggaagatg ctgcagttgg      60
gcaaggtcag gaccttgcct tgaaagccgg gcggcgccgc gcaacgcctc ttcccggact     120
gaggagctgt cgccggcgga gggtgcatgt ttgcgaggaa gccgccgggc gccgcgcctt     180
tgggagctat gcctgttcca gaccagcctt catcagcctc agagaagacg agttccctga     240
gccccggctt aaacacctcc aacggggatg gctctgaaac agaaaccacc tctgccatcc     300
tcgcctcagt caaagaacag gaattacagt ttgaaaggct gacccgagag ctggaggctg     360
aacggcagat cgtagccagc cagctggagc gatgcaagct cggatccgag actggcagca     420
tgagcagcat gagttcagca agagcagtt ttcagtggga gtcacaagat ggtcaaaaag      480
atatcgaaga tgagcttaca acaggtctcg agctggtgga ctcctgtatt aggtcactac     540
aggaatcagg aatacttgac ccacaggatt attctacagg tgaaaggccc agcctgctct     600
cccagagtgc acttcagctc aattccaaac ctgaagggtc tttccagtat ccggccagct     660
accatagcaa ccagaccctg gcctgggggg aaaccacccc ttcacagctc ccggcccgag     720
gcacacaagc ccgagctacg ggccagagct tcagccaggg cacgaccagc cgcgccggcc     780
acctggcggg gcccgagccc gcgccgccgc cgccgccgcc gccgcgggag ccgttcgcgc     840
ccagcctggg cagcgccttc cacctgcccg acgcgccgcc cgccgccgcc gccgccgcgc     900
tctactactc cagctccacg ctgcccgcgc cgccgcgcgg gggctccccg ctggccgcgc     960
cccagggcgg ttcgcccacc aagctgcagc gcggcggctc ggcccccgag ggcgccacct    1020
acgccgcgcc gcgcggctcc tcgcccaagc agtcgcccag ccgcctggcc aagtcctaca    1080
gcaccagctc gcccatcaac atcgtcgtgt cctcggccgg cctgtccccg atccgcgtga    1140
cctcgccccc caccgtgcag tccaccatct cctcctcgcc catccaccag ctgagctcca    1200
ccatcggcac gtacgccacc ctgtcgccca ccaagcgcct ggtccacgcg tccgagcagt    1260
acagcaagca ctcgcaggag ctgtatgcca cggccaccct ccagaggccg ggcagcctgg    1320
cagctggttc ccgagcctca tacagcagcc agcatgggca cctgggccca gagttgcggg    1380
ccctgcagtc cccagaacac cacatagatc ccatctatga agaccgcgtc tatcagaagc    1440
ccccctatgag gagtctcagc cagagccagg gggaccctct gccgccagca cacaccggca    1500
cctaccgcac gagcacagcc ccatcttccc ctggtgtcga ctccgtcccc ttgcagcgca    1560
caggcagcca gcacggccca cagaatgccg ccgcggccac cttccagagg gccagctatg    1620
ccgccggccc agcctccaat tacgcggacc cctaccgaca gctgcagtat tgtcccctctg    1680
ttgagtctcc atacagcaaa tccggccctg ctctcccgcc tgaaggcacc ttggccaggt    1740
ccccgtccat tgatagcatt cagaaagatc ccagagaatt tggatggaga gacccggaac    1800
tgccggaagt gattcagatg ttgcagcacc agtttccctc ggtccagtct aacgcggcag    1860
cctacttgca acacctctgt tttgagaca acaaaattaa agccgagata aggagacaag    1920
gaggcatcca gctcctggtg gacctgttgg atcatcggat gaccgaagtc caccgtagtg    1980
cctgtggagc tctgagaaac ctggtgtatg gaaggccaa cgatgataac aaaattgccc     2040
tgaaaaactg tggtggcatc ccagcactgg tgaggttact ccgcaagacg actgacctgg    2100
agatccggga gctggtcaca ggagtccttt ggaacctctc ctcatgcgat gcactcaaaa    2160
tgccaatcat ccaggatgcc ctagcagtac tgaccaacgc ggtgattatc ccccactcag    2220
gctgggaaaa ttcgcctctt caggatgatc ggaaaataca gctgcattca tcacaggtgc    2280
tgcgtaacgc caccgggtgc ctaaggaatg ttagttcggc cggagaggag gcccgcaaaa    2340
ggatgagaga gtgtgatggg cttacggatg ccttgctgta cgtgatccag tctgcgctgg    2400
```

-continued

```
ggagcagtga gatcgatagc aagaccgttg aaaactgtgt gtgcatttta aggaacctct    2460
cgtaccggct ggcggcagaa acgtctcagg gacagcacat gggcacggac gagctggacg    2520
ggctactctg tggcgaggcc aatggcaagg atgctgagag ctctgggtgc tggggcaaga    2580
agaagaagaa aaagaaatcc aagatcagt gggatggagt aggacctctt ccagactgtg    2640
ctgaaccacc aaaagggatc cagatgctgt ggcacccatc aatagtcaaa ccctacctca    2700
cactgctctc tgagtgctca atccagaca cgctggaagg ggcggcaggc gccctgcaga    2760
acttggctgc agggagctgg aagtggtcag tatatatccg agccgctgtc cgaaaagaga    2820
aaggcctgcc catcctcgtg gagctgctcc gaatagacaa tgaccgtgtg gtgtgcgcgg    2880
tggccactgc gctgcggaac atggccttgg acgtcagaaa taaggagctc atcggcaaat    2940
acgccatgcg agacctagtc cacaggcttc caggagggaa caacagcaac aacactgcaa    3000
gcaaggccat gtcggatgac acagtgacag ctgtctgctg cacactgcac gaagtgatta    3060
ccaagaacat ggagaacgcc aaggccttac gggatgccgg tggcatcgag aagttggtcg    3120
gcatctccaa aagcaaagga gataaacact ctccaaaagt ggtcaaggct gcatctcagg    3180
tcctcaacag catgtggcag taccgagatc tgaggagtct ctacaaaaag gatggatggt    3240
cacaatacca ctttgtagcc tcgtcttcaa ccatcgagag ggaccggcaa aggccctact    3300
cctcctcccg cacgccctcc atctcccctg tgcgcgtgtc tcccaacaac cgctcagcaa    3360
gtgccccagc ttcacctcgg gaaatgatca gcctcaaaga aaggaaaaca gactacgagt    3420
gcaccggcag caacgccacc taccacggag ctaaaggcga acacacttcc aggaaagatg    3480
ccatgacagc tcaaaacact ggaatttcaa cttttgtatag gaattcttat ggtgcgcccg    3540
ctgaagacat caaacacaac caggtttcag cacagccagt cccacaggag cccagcagaa    3600
aagattacga gacctaccag ccatttcaga attccacaag aaattacgat gagtccttct    3660
tcgaggacca ggtccaccat cgccctcccg ccagcgagta caccatgcac ctgggtctca    3720
agtccaccgg caactacgtt gacttctact cagctgcccg tccctacagt gaactgaact    3780
atgaaacgag ccactacccg gcctcccccg actcctgggt gtgaggagca gggcacaggc    3840
gctccgggaa cagtgcatgt gcatgcatac cacaagacat ttctttctgt tttgttttt    3900
tctcctgcaa atttagtttg ttaaagcctg ttccatagga aggctgtgat aaccagtaag    3960
gaaatattaa gagctatttt agaaagctaa atgaatcgca agttaacttg gaaatcagta    4020
gaaagctaaa gtgatcctaa atatgacagt gggcagcacc tttctagcgt gagctgtaaa    4080
gtaacgagaa gtgctttata ctgaacgtgg ttgatgggag gagagacgag gcattcgggc    4140
cggtggggcg taagggttat cgttaagcac aagacacaga atagtttaca cactgtgtgg    4200
gggacggctt ctcacgcttt gtttactctc ttcatccgtt gtgactctag gcttcaggtt    4260
gcattgggt tcctctgtac agcaagatgt ttcttgcctt tgttaatgc attgttgtaa    4320
agtatttgat gtacattaca gattaaagaa gaaaagcgcg ttgtgtatat tacaccaatg    4380
ccgccgtgtt tcctcatcta tggttctaaa tattgcttca atttcaaact tttgaaagat    4440
gtatggattt ccagtttttc tttactttct cccagtatgt tttaacaaaa aaaaaaaaa    4500
gcaggaaaaa aggaatattt agcagtattg ttcgttctga tatgtgaatt tgtttgtgac    4560
aactaaacaa ggcattcagc agtttctgac aattaacata catcattcca cactccttgt    4620
caacaaagtg cttttttcact gcctaaaatt ttagatgtag atatttgaaa tagatttttt    4680
catttatacc agttttcttt atgatgatac agtgttaaaa gaaaataaat tacaattgat    4740
``` ctgtca                                                          4746

<210> SEQ ID NO 4
<211> LENGTH: 1225
<212> TYPE: PRT
<213> ORGANISM: human

<400> SEQUENCE: 4

Met Phe Ala Arg Lys Pro Pro Gly Ala Ala Pro Leu Gly Ala Met Pro
1               5                   10                  15

Val Pro Asp Gln Pro Ser Ser Ala Ser Glu Lys Thr Ser Ser Leu Ser
            20                  25                  30

Pro Gly Leu Asn Thr Ser Asn Gly Asp Gly Ser Glu Thr Glu Thr Thr
        35                  40                  45

Ser Ala Ile Leu Ala Ser Val Lys Glu Gln Glu Leu Gln Phe Glu Arg
    50                  55                  60

Leu Thr Arg Glu Leu Glu Ala Glu Arg Gln Ile Val Ala Ser Gln Leu
65                  70                  75                  80

Glu Arg Cys Lys Leu Gly Ser Glu Thr Gly Ser Met Ser Ser Met Ser
                85                  90                  95

Ser Ala Glu Glu Gln Phe Gln Trp Gln Ser Gln Asp Gly Gln Lys Asp
            100                 105                 110

Ile Glu Asp Glu Leu Thr Thr Gly Leu Glu Leu Val Asp Ser Cys Ile
        115                 120                 125

Arg Ser Leu Gln Glu Ser Gly Ile Leu Asp Pro Gln Asp Tyr Ser Thr
    130                 135                 140

Gly Glu Arg Pro Ser Leu Leu Ser Gln Ser Ala Leu Gln Leu Asn Ser
145                 150                 155                 160

Lys Pro Glu Gly Ser Phe Gln Tyr Pro Ala Ser Tyr His Ser Asn Gln
                165                 170                 175

Thr Leu Ala Leu Gly Glu Thr Thr Pro Ser Gln Leu Pro Ala Arg Gly
            180                 185                 190

Thr Gln Ala Arg Ala Thr Gly Gln Ser Phe Ser Gln Gly Thr Thr Ser
        195                 200                 205

Arg Ala Gly His Leu Ala Gly Pro Glu Pro Ala Pro Pro Pro Pro
    210                 215                 220

Pro Pro Arg Glu Pro Phe Ala Pro Ser Leu Gly Ser Ala Phe His Leu
225                 230                 235                 240

Pro Asp Ala Pro Pro Ala Ala Ala Ala Ala Leu Tyr Tyr Ser Ser
                245                 250                 255

Ser Thr Leu Pro Ala Pro Pro Arg Gly Gly Ser Pro Leu Ala Ala Pro
            260                 265                 270

Gln Gly Gly Ser Pro Thr Lys Leu Gln Arg Gly Gly Ser Ala Pro Glu
        275                 280                 285

Gly Ala Thr Tyr Ala Ala Pro Arg Gly Ser Ser Pro Lys Gln Ser Pro
    290                 295                 300

Ser Arg Leu Ala Lys Ser Tyr Ser Thr Ser Ser Pro Ile Asn Ile Val
305                 310                 315                 320

Val Ser Ser Ala Gly Leu Ser Pro Ile Arg Val Thr Ser Pro Pro Thr
                325                 330                 335

Val Gln Ser Thr Ile Ser Ser Pro Ile His Gln Leu Ser Ser Thr
            340                 345                 350

Ile Gly Thr Tyr Ala Thr Leu Ser Pro Thr Lys Arg Leu Val His Ala
        355                 360                 365

-continued

```
Ser Glu Gln Tyr Ser Lys His Ser Gln Glu Leu Tyr Ala Thr Ala Thr
    370                 375                 380

Leu Gln Arg Pro Gly Ser Leu Ala Ala Gly Ser Arg Ala Ser Tyr Ser
385                 390                 395                 400

Ser Gln His Gly His Leu Gly Pro Glu Leu Arg Ala Leu Gln Ser Pro
                405                 410                 415

Glu His His Ile Asp Pro Ile Tyr Glu Asp Arg Val Tyr Gln Lys Pro
            420                 425                 430

Pro Met Arg Ser Leu Ser Gln Ser Gln Gly Asp Pro Leu Pro Pro Ala
        435                 440                 445

His Thr Gly Thr Tyr Arg Thr Ser Thr Ala Pro Ser Ser Pro Gly Val
    450                 455                 460

Asp Ser Val Pro Leu Gln Arg Thr Gly Ser Gln His Gly Pro Gln Asn
465                 470                 475                 480

Ala Ala Ala Ala Thr Phe Gln Arg Ala Ser Tyr Ala Ala Gly Pro Ala
                485                 490                 495

Ser Asn Tyr Ala Asp Pro Tyr Arg Gln Leu Gln Tyr Cys Pro Ser Val
            500                 505                 510

Glu Ser Pro Tyr Ser Lys Ser Gly Pro Ala Leu Pro Pro Glu Gly Thr
        515                 520                 525

Leu Ala Arg Ser Pro Ser Ile Asp Ser Ile Gln Lys Asp Pro Arg Glu
    530                 535                 540

Phe Gly Trp Arg Asp Pro Glu Leu Pro Glu Val Ile Gln Met Leu Gln
545                 550                 555                 560

His Gln Phe Pro Ser Val Gln Ser Asn Ala Ala Ala Tyr Leu Gln His
                565                 570                 575

Leu Cys Phe Gly Asp Asn Lys Ile Lys Ala Glu Ile Arg Arg Gln Gly
            580                 585                 590

Gly Ile Gln Leu Leu Val Asp Leu Leu Asp His Arg Met Thr Glu Val
        595                 600                 605

His Arg Ser Ala Cys Gly Ala Leu Arg Asn Leu Val Tyr Gly Lys Ala
    610                 615                 620

Asn Asp Asp Asn Lys Ile Ala Leu Lys Asn Cys Gly Gly Ile Pro Ala
625                 630                 635                 640

Leu Val Arg Leu Leu Arg Lys Thr Thr Asp Leu Glu Ile Arg Glu Leu
                645                 650                 655

Val Thr Gly Val Leu Trp Asn Leu Ser Ser Cys Asp Ala Leu Lys Met
            660                 665                 670

Pro Ile Ile Gln Asp Ala Leu Ala Val Leu Thr Asn Ala Val Ile Ile
        675                 680                 685

Pro His Ser Gly Trp Glu Asn Ser Pro Leu Gln Asp Asp Arg Lys Ile
    690                 695                 700

Gln Leu His Ser Ser Gln Val Leu Arg Asn Ala Thr Gly Cys Leu Arg
705                 710                 715                 720

Asn Val Ser Ser Ala Gly Glu Glu Ala Arg Arg Arg Met Arg Glu Cys
                725                 730                 735

Asp Gly Leu Thr Asp Ala Leu Leu Tyr Val Ile Gln Ser Ala Leu Gly
            740                 745                 750

Ser Ser Glu Ile Asp Ser Lys Thr Val Glu Asn Cys Val Cys Ile Leu
        755                 760                 765

Arg Asn Leu Ser Tyr Arg Leu Ala Ala Glu Thr Ser Gln Gly Gln His
    770                 775                 780

Met Gly Thr Asp Glu Leu Asp Gly Leu Leu Cys Gly Glu Ala Asn Gly
```

-continued

```
            785                 790                 795                 800
Lys Asp Ala Glu Ser Ser Gly Cys Trp Gly Lys Lys Lys Lys Lys Lys
                    805                 810                 815

Lys Ser Gln Asp Gln Trp Asp Gly Val Gly Pro Leu Pro Asp Cys Ala
            820                 825                 830

Glu Pro Pro Lys Gly Ile Gln Met Leu Trp His Pro Ser Ile Val Lys
            835                 840                 845

Pro Tyr Leu Thr Leu Leu Ser Glu Cys Ser Asn Pro Asp Thr Leu Glu
            850                 855                 860

Gly Ala Ala Gly Ala Leu Gln Asn Leu Ala Ala Gly Ser Trp Lys Trp
865                 870                 875                 880

Ser Val Tyr Ile Arg Ala Ala Val Arg Lys Glu Lys Gly Leu Pro Ile
                    885                 890                 895

Leu Val Glu Leu Leu Arg Ile Asp Asn Asp Arg Val Val Cys Ala Val
            900                 905                 910

Ala Thr Ala Leu Arg Asn Met Ala Leu Asp Val Arg Asn Lys Glu Leu
            915                 920                 925

Ile Gly Lys Tyr Ala Met Arg Asp Leu Val His Arg Leu Pro Gly Gly
    930                 935                 940

Asn Asn Ser Asn Asn Thr Ala Ser Lys Ala Met Ser Asp Asp Thr Val
945                 950                 955                 960

Thr Ala Val Cys Cys Thr Leu His Glu Val Ile Thr Lys Asn Met Glu
                    965                 970                 975

Asn Ala Lys Ala Leu Arg Asp Ala Gly Gly Ile Glu Lys Leu Val Gly
            980                 985                 990

Ile Ser Lys Ser Lys Gly Asp Lys His Ser Pro Lys Val Val Lys Ala
    995                 1000                1005

Ala Ser Gln Val Leu Asn Ser Met Trp Gln Tyr Arg Asp Leu Arg Ser
    1010                1015                1020

Leu Tyr Lys Lys Asp Gly Trp Ser Gln Tyr His Phe Val Ala Ser Ser
1025                1030                1035                1040

Ser Thr Ile Glu Arg Asp Arg Gln Arg Pro Tyr Ser Ser Ser Arg Thr
                    1045                1050                1055

Pro Ser Ile Ser Pro Val Arg Val Ser Pro Asn Asn Arg Ser Ala Ser
            1060                1065                1070

Ala Pro Ala Ser Pro Arg Glu Met Ile Ser Leu Lys Glu Arg Lys Thr
            1075                1080                1085

Asp Tyr Glu Cys Thr Gly Ser Asn Ala Thr Tyr His Gly Ala Lys Gly
            1090                1095                1100

Glu His Thr Ser Arg Lys Asp Ala Met Thr Ala Gln Asn Thr Gly Ile
1105                1110                1115                1120

Ser Thr Leu Tyr Arg Asn Ser Tyr Gly Ala Pro Ala Glu Asp Ile Lys
                    1125                1130                1135

His Asn Gln Val Ser Ala Gln Pro Val Pro Gln Glu Pro Ser Arg Lys
            1140                1145                1150

Asp Tyr Glu Thr Tyr Gln Pro Phe Gln Asn Ser Thr Arg Asn Tyr Asp
            1155                1160                1165

Glu Ser Phe Phe Glu Asp Gln Val His His Arg Pro Pro Ala Ser Glu
            1170                1175                1180

Tyr Thr Met His Leu Gly Leu Lys Ser Thr Gly Asn Tyr Val Asp Phe
1185                1190                1195                1200

Tyr Ser Ala Ala Arg Pro Tyr Ser Glu Leu Asn Tyr Glu Thr Ser His
                    1205                1210                1215
```

Tyr Pro Ala Ser Pro Asp Ser Trp Val
           1220                  1225

<210> SEQ ID NO 5
<211> LENGTH: 4998
<212> TYPE: DNA
<213> ORGANISM: mouse

<400> SEQUENCE: 5

| | | | | | |
|---|---|---|---|---|---|
| aagcgccgga | gccggccgcc | gcggctgagc | cggaggctga | gctgcggcgc | gcggcgggag | 60 |
| gagcctcgct | ctcggcggcg | gcggcggcgg | cggcgacaca | ggtggcgcgg | gcggcgcgca | 120 |
| gggcgcagct | cgagagcgct | cggcgccggg | cgccagggcg | gcccaggctc | gcgcccgcgg | 180 |
| cggcaaccgg | ccgagcggag | cggcgggcgc | ggcggctcgg | tagcccggcc | cgagcccggg | 240 |
| gagccccgcg | gaaccctgag | catcccgcgg | cgcccgccga | gtcgggcagg | gggcgctacg | 300 |
| ctcgccgcgc | tcgagggggc | ggccgggccg | ggcgctgcgc | actcgcgtcg | ggagccgcct | 360 |
| ctcgcctgcc | gcgctcgccc | tgctccccg | ccagcatcac | ttgtcccgcg | gccgcgctcc | 420 |
| gacaacaaaa | gcgaggatg | ctgcagctgg | gcaaggtcag | gaccttgctc | tgaagccggg | 480 |
| cggcggcgcg | cacgcctttc | ccccgactga | ggagctgtct | ttggcggcgg | gtgcatgttc | 540 |
| gccaggaagc | agtcgggcgc | cgcgccgttc | ggagctatgc | ctgtcccaga | ccagcctcca | 600 |
| tcagcctcag | agaagaacag | ctccttgagc | ccaggcttaa | acacctccaa | tggtgatggc | 660 |
| tctgagacga | aaaccacctc | tgctatcctt | gcctccgtca | agaacagga | attacagttt | 720 |
| gaaaggctga | cccgagagct | ggaggctgaa | cgccagatcg | tagccagcca | gctggagcga | 780 |
| tgcaagcttg | gctcggagac | aggaagcatg | agcagtatca | gttcagcagg | agagcagttt | 840 |
| cactggcaga | cacaagatgg | ccaaaaagat | atcgaagatg | aacttacaac | gggccttgag | 900 |
| ctggtggact | cctgtatccg | ctctctgcag | gagtcaggca | ttctggaccc | acaggattac | 960 |
| tccacaagtg | aaaggcctag | cctgctctcc | cagagtgcac | ttcagctcaa | ttctaaacct | 1020 |
| gaagggtctt | tccagtatcc | ggccagctac | catagcaacc | agaccctggc | cctgggtgac | 1080 |
| acagccccct | tctcagctccc | agcacgcagc | acgaagccc | gagctgccgg | ccagagcttc | 1140 |
| agccagggca | cgaccggccg | cgcggggcac | ctggcgggct | ccgagcctgc | gccaccgcct | 1200 |
| ccgcctccgc | gggaaccgtt | cgcgcccagc | ctgggcagcg | ccttccacct | gcccgacgcg | 1260 |
| ccgcccgccg | ccgcggcgct | ctactactcc | agtccacgc | tgcccgcgcc | gcgcgcgggg | 1320 |
| ggctccccgc | tgaccaccac | gcagggcggc | tcacccacca | agctgcagcg | cggaggctcg | 1380 |
| gcccccgagg | gtgccgccta | cgccgcgccg | cgcggctcct | cgcccaagca | gtcgcccagc | 1440 |
| cgcctggcta | agtcctacag | caccagctcg | cccatcaaca | tcgtcgtgtc | ctcggccggc | 1500 |
| ctgtccccga | tccgcgtgac | ctcgcccccc | accgtgcagt | ccaccatctc | ctcttcgccc | 1560 |
| atccaccagc | tgagctccac | catcggcacc | tacgccaccc | tgtcgcccac | caagcgcctg | 1620 |
| gtccacgcgt | ctgagcagta | cagcaagcat | tcgcaggagc | tgtatgccac | cgccaccctc | 1680 |
| cagaggccgg | gcagcctggc | agctggatcc | cgagcctcgt | atagcagcca | gcatgggcac | 1740 |
| ctggccctg | agctgcgggc | cctgcagtcc | ccagagcacc | acatagaccc | catctatgaa | 1800 |
| gaccgtgtct | atcagaagcc | ccctatgagg | agtctcagcc | agagccaggg | ggatcctctg | 1860 |
| ccgccagcac | ataccggcac | cttccgcacg | agcacagccc | cgtcctcccc | tggtgtcgac | 1920 |
| tccgtccccct | tgcagcgcac | aggcagccaa | cacgggccac | agaatgccgc | cgcagccacc | 1980 |
| ttccagaggg | ccagctatgc | tgccggccca | gcctccaact | acgcagaccc | ctaccgacag | 2040 |

-continued

```
ctgcagtatt gtgcctccgt tgactctccg tacagcaaat ctggccctgc cctcccaccc      2100
gaaggcacct tggccagatc cccatccatc gacagcattc agaaagaccc cagggagttt      2160
ggatggagag acccggagct gcctgaagtg atacagatgt tacagcacca gttcccttca      2220
gtccagtcca atgctgcagc ttacctgcaa cacctctgtt ttggagacaa taaaattaag      2280
gcagagataa ggagacaagg aaggatacag ctcctggtgg acctgctgga tcaccgaatg      2340
acagaagtcc accgtagtgc ctgtggggct ctgaggaacc tggtgtatgg aaggccaat       2400 gatgataaca aaatcgccct gaaaaactgt ggtggtatcc cagcgctggt gagactcctt      2460
cgcaagacca cagacctgga gatccgggag ctggtcacag gagtcctttg gaacctctca      2520
tcatgtgatg cactcaaaat gccaatcatc caggacgccc tggcagtgct gaccaatgcg      2580
gtgattatcc ctcactcggg ctgggagaat tcacctcttc aggatgatcg gaaaatacag      2640
ctgcattcat cacaggtgct gcgcaacgcc actgggtgcc taaggaatgt aagttcagct      2700
ggagaggagg cccgccgaag gatgcgggag tgtgatgggc tcacggatgc cttgctgtac      2760
gtgatccagt ctgcactggg gagcagtgag atcgatagca agaccgttga aaactgtgtg      2820
tgcatcttga ggaacctctc ctaccggcta gcagcagaaa cgtctcaggg acagcacatg      2880
ggcacagacg agctggacgg gctgctctgc ggggagacca acggcaaaga cacagagagt      2940
tctgggtgct ggggcaagaa gaagaagaaa aagaaatccc aggaccagtg ggatggagta      3000
ggacctcttc cagactgtgc agagccacca aaagggatcc agatgctgtg gcacccgtcc      3060
atagtcaaac cctacctcac actgctctct gagtgctcaa acccagacac gctggaaggg      3120
gcagcgggcg ccctgcagaa cttggctgca gggagctgga agggctgggc tgaggatgtg      3180
gcaggcatgg cgtatgccct acgttcactg ccagaggggg ctccctgcct gccacagtgg      3240
tccgtgtata tccgagctgc tgtccggaaa gagaaaggcc tgcccattct tgtggagctc      3300
ctccgaatag acaatgaccg tgtagtgtgt gcagtggcca cagcacttcg gaacatggcc      3360
ctcgatgtca gaaacaagga actcattggc aagtatgcca tgcgagacct ggtccaccgg      3420
cttcctggtg ggaacaacag caacaactcg gggagcaagg ccatgtcaga tgacaccgtg      3480
acggccgtgt gctgcaccct gcatgaagtg atcaccaaga acatggagaa tgccaaggcc      3540
ttacgggatg ctggtggcat cgagaagttg gtcggcatct ctaaaagcaa aggagacaag      3600
cactctccaa aggtggtcaa ggctgcttct caggtcctaa acagcatgtg gcagtatcgc      3660
gatctgagga gtctctacaa gaaggatgga tggtcacaat atcactttgt agcctcatct      3720
tcaaccatcg agagggatcg acaaaggccc tactcctcct cccgcacacc ctccatctct      3780
cccgtgcgtt tgtctcccaa caaccgctca gcaagtgccc cagcttcacc tcgggaaatg      3840
atcagcctca agaaaggaa gacggactac gagtccgctg gcaacaacgc cacttaccac      3900
ggaactaaag gagaacacac ctccagaaaa gacaccatga cagctcaaaa cactggagtt      3960
tcaactttgt acaggaattc atacggtgcg cccgctgaag acatcaaaca gaaccaggtt      4020
tccacacagc ctgtccctca ggagcccagc aggaaagact cgagacccta ccagcccttt      4080
ccgaattcca cacgaaatta tgatgagtcc ttctttgagg accaggtcca ccaccgccct      4140
ccagccagcg agtacaccat gcacctgggc ctcaagtcca ctgcaacta tgtcgacttc      4200 tactctgcag cccgtcctta cagtgaactg aactatgaaa cgagccacta cccggcctcg      4260
cccgactcct gggtgtaagg agccaggaca cgaggcactc cggggacagt gcatgtgcat      4320
gcatacacca caggacattt tgtttctttt tttcttttct tttctttttgt tttttttttt      4380
```

| | | |
|---|---|---|
| ttttctttcc ctgcaaattt agtttgttaa agcctgttcc gtaggaaggc tgtgataacc | 4440 |
| aggaagaaat actcagagct attttagaaa gctaaaatga atcaagagtt aactgggaaa | 4500 |
| tcgataggaa gctaaacgca atcctaattg tgaccgcatt caacacctttt ctagtttgaa | 4560 |
| ctatagcatt ttgaaagtgc tttatagtcc ggtgaggctg aagtaggag agaggagaca | 4620 |
| gtcaggtgg tgggcgtggt tatcgctaag cacaagacag actagtttac acactgtggg | 4680 |
| gacggcttct cacgctttgt ttactctctt catccgtgtg actctaggct tcaagttgca | 4740 |
| ttgggttcc tctgtacagc aagacgtctc ttgccttttg ttaatgcatt gttgtaaagt | 4800 |
| attcgatgta cattacagat aaagacgaa gagtgcattg tgtatattac accaatgcca | 4860 |
| ctgtgtttcc tcatcaatgg ttctaaatat tgcttcaatt tcaaactttt gaaagatgta | 4920 |
| tgggtttcca attttctttt tttttttctt tctcccagta tgttttaaca aaaaggaaa | 4980 |
| aaaaaaacag gaaaaaaa | 4998 |

<210> SEQ ID NO 6
<211> LENGTH: 1247
<212> TYPE: PRT
<213> ORGANISM: mouse

<400> SEQUENCE: 6

```
Met Phe Ala Arg Lys Gln Ser Gly Ala Ala Pro Phe Gly Ala Met Pro
1               5                   10                  15

Val Pro Asp Gln Pro Pro Ser Ala Ser Glu Lys Asn Ser Ser Leu Ser
            20                  25                  30

Pro Gly Leu Asn Thr Ser Asn Gly Asp Gly Ser Glu Thr Glu Thr Thr
        35                  40                  45

Ser Ala Ile Leu Ala Ser Val Lys Glu Gln Glu Leu Gln Phe Glu Arg
    50                  55                  60

Leu Thr Arg Glu Leu Glu Ala Glu Arg Gln Ile Val Ala Ser Gln Leu
65                  70                  75                  80

Glu Arg Cys Lys Leu Gly Ser Glu Thr Gly Ser Met Ser Ser Ile Ser
                85                  90                  95

Ser Ala Gly Glu Gln Phe His Trp Gln Thr Gln Asp Gly Gln Lys Asp
            100                 105                 110

Ile Glu Asp Glu Leu Thr Thr Gly Leu Glu Leu Val Asp Ser Cys Ile
        115                 120                 125

Arg Ser Leu Gln Glu Ser Gly Ile Leu Asp Pro Gln Asp Tyr Ser Thr
    130                 135                 140

Ser Glu Arg Pro Ser Leu Leu Ser Gln Ser Ala Leu Gln Leu Asn Ser
145                 150                 155                 160

Lys Pro Glu Gly Ser Phe Gln Tyr Pro Ala Ser Tyr His Ser Asn Gln
                165                 170                 175

Thr Leu Ala Leu Gly Asp Thr Ala Pro Ser Gln Leu Pro Ala Arg Ser
            180                 185                 190

Thr Gln Ala Arg Ala Ala Gly Gln Ser Phe Ser Gln Gly Thr Thr Gly
        195                 200                 205

Arg Ala Gly His Leu Ala Gly Ser Glu Pro Ala Pro Pro Pro Pro Pro
    210                 215                 220

Pro Arg Glu Pro Phe Ala Pro Ser Leu Gly Ser Ala Phe His Leu Pro
225                 230                 235                 240

Asp Ala Pro Pro Ala Ala Ala Leu Tyr Tyr Ser Ser Ser Thr Leu
                245                 250                 255

Pro Ala Pro Pro Arg Gly Gly Ser Pro Leu Thr Thr Thr Gln Gly Gly
```

-continued

```
                    260                 265                 270
Ser Pro Thr Lys Leu Gln Arg Gly Gly Ser Ala Pro Glu Gly Ala Ala
            275                 280                 285
Tyr Ala Ala Pro Arg Gly Ser Ser Pro Lys Gln Ser Pro Ser Arg Leu
        290                 295                 300
Ala Lys Ser Tyr Ser Thr Ser Ser Pro Ile Asn Ile Val Val Ser Ser
305                 310                 315                 320
Ala Gly Leu Ser Pro Ile Arg Val Thr Ser Pro Thr Val Gln Ser
                325                 330                 335
Thr Ile Ser Ser Pro Ile His Gln Leu Ser Ser Thr Ile Gly Thr
            340                 345                 350
Tyr Ala Thr Leu Ser Pro Thr Lys Arg Leu Val His Ala Ser Glu Gln
            355                 360                 365
Tyr Ser Lys His Ser Gln Glu Leu Tyr Ala Thr Ala Thr Leu Gln Arg
        370                 375                 380
Pro Gly Ser Leu Ala Ala Gly Ser Arg Ala Ser Tyr Ser Ser Gln His
385                 390                 395                 400
Gly His Leu Ala Pro Glu Leu Arg Ala Leu Gln Ser Pro Glu His His
                405                 410                 415
Ile Asp Pro Ile Tyr Glu Asp Arg Val Tyr Gln Lys Pro Pro Met Arg
                420                 425                 430
Ser Leu Ser Gln Ser Gln Gly Asp Pro Leu Pro Pro Ala His Thr Gly
            435                 440                 445
Thr Phe Arg Thr Ser Thr Ala Pro Ser Ser Pro Gly Val Asp Ser Val
        450                 455                 460
Pro Leu Gln Arg Thr Gly Ser Gln His Gly Pro Gln Asn Ala Ala Ala
465                 470                 475                 480
Ala Thr Phe Gln Arg Ala Ser Tyr Ala Ala Gly Pro Ala Ser Asn Tyr
                485                 490                 495
Ala Asp Pro Tyr Arg Gln Leu Gln Tyr Cys Ala Ser Val Asp Ser Pro
            500                 505                 510
Tyr Ser Lys Ser Gly Pro Ala Leu Pro Pro Glu Gly Thr Leu Ala Arg
        515                 520                 525
Ser Pro Ser Ile Asp Ser Ile Gln Lys Asp Pro Arg Glu Phe Gly Trp
530                 535                 540
Arg Asp Pro Glu Leu Pro Glu Val Ile Gln Met Leu Gln His Gln Phe
545                 550                 555                 560
Pro Ser Val Gln Ser Asn Ala Ala Ala Tyr Leu Gln His Leu Cys Phe
                565                 570                 575
Gly Asp Asn Lys Ile Lys Ala Glu Ile Arg Arg Gln Gly Gly Ile Gln
            580                 585                 590
Leu Leu Val Asp Leu Leu Asp His Arg Met Thr Glu Val His Arg Ser
        595                 600                 605
Ala Cys Gly Ala Leu Arg Asn Leu Val Tyr Gly Lys Ala Asn Asp Asp
        610                 615                 620
Asn Lys Ile Ala Leu Lys Asn Cys Gly Gly Ile Pro Ala Leu Val Arg
625                 630                 635                 640
Leu Leu Arg Lys Thr Thr Asp Leu Glu Ile Arg Glu Leu Val Thr Gly
                645                 650                 655
Val Leu Trp Asn Leu Ser Ser Cys Asp Ala Leu Lys Met Pro Ile Ile
                660                 665                 670
Gln Asp Ala Leu Ala Val Leu Thr Asn Ala Val Ile Ile Pro His Ser
            675                 680                 685
```

```
Gly Trp Glu Asn Ser Pro Leu Gln Asp Asp Arg Lys Ile Gln Leu His
    690             695                 700

Ser Ser Gln Val Leu Arg Asn Ala Thr Gly Cys Leu Arg Asn Val Ser
705                 710                 715                 720

Ser Ala Gly Glu Glu Ala Arg Arg Arg Met Arg Glu Cys Asp Gly Leu
            725                 730                 735

Thr Asp Ala Leu Leu Tyr Val Ile Gln Ser Ala Leu Gly Ser Ser Glu
        740                 745                 750

Ile Asp Ser Lys Thr Val Glu Asn Cys Val Cys Ile Leu Arg Asn Leu
        755                 760                 765

Ser Tyr Arg Leu Ala Ala Glu Thr Ser Gln Gly Gln His Met Gly Thr
    770                 775                 780

Asp Glu Leu Asp Gly Leu Leu Cys Gly Glu Thr Asn Gly Lys Asp Thr
785                 790                 795                 800

Glu Ser Ser Gly Cys Trp Gly Lys Lys Lys Lys Lys Lys Ser Gln
            805                 810                 815

Asp Gln Trp Asp Gly Val Gly Pro Leu Pro Asp Cys Ala Glu Pro Pro
            820                 825                 830

Lys Gly Ile Gln Met Leu Trp His Pro Ser Ile Val Lys Pro Tyr Leu
        835                 840                 845

Thr Leu Leu Ser Glu Cys Ser Asn Pro Asp Thr Leu Glu Gly Ala Ala
    850                 855                 860

Gly Ala Leu Gln Asn Leu Ala Ala Gly Ser Trp Lys Gly Trp Ala Glu
865                 870                 875                 880

Asp Val Ala Gly Met Ala Tyr Ala Leu Arg Ser Leu Pro Glu Gly Ala
            885                 890                 895

Pro Cys Leu Pro Gln Trp Ser Val Tyr Ile Arg Ala Ala Val Arg Lys
        900                 905                 910

Glu Lys Gly Leu Pro Ile Leu Val Glu Leu Leu Arg Ile Asp Asn Asp
        915                 920                 925

Arg Val Val Cys Ala Val Ala Thr Ala Leu Arg Asn Met Ala Leu Asp
930                 935                 940

Val Arg Asn Lys Glu Leu Ile Gly Lys Tyr Ala Met Arg Asp Leu Val
945                 950                 955                 960

His Arg Leu Pro Gly Gly Asn Asn Ser Asn Asn Ser Gly Ser Lys Ala
            965                 970                 975

Met Ser Asp Asp Thr Val Thr Ala Val Cys Cys Thr Leu His Glu Val
            980                 985                 990

Ile Thr Lys Asn Met Glu Asn Ala Lys Ala Leu Arg Asp Ala Gly Gly
        995                 1000                1005

Ile Glu Lys Leu Val Gly Ile Ser Lys Ser Lys Gly Asp Lys His Ser
    1010                1015                1020

Pro Lys Val Val Lys Ala Ala Ser Gln Val Leu Asn Ser Met Trp Gln
1025                1030                1035                1040

Tyr Arg Asp Leu Arg Ser Leu Tyr Lys Lys Asp Gly Trp Ser Gln Tyr
            1045                1050                1055

His Phe Val Ala Ser Ser Thr Ile Glu Arg Asp Arg Gln Arg Pro
            1060                1065                1070

Tyr Ser Ser Ser Arg Thr Pro Ser Ile Ser Pro Val Arg Val Ser Pro
            1075                1080                1085

Asn Asn Arg Ser Ala Ser Ala Pro Ala Ser Pro Arg Glu Met Ile Ser
1090                1095                1100
```

```
Leu Lys Glu Arg Lys Thr Asp Tyr Glu Ser Ala Gly Asn Asn Ala Thr
1105                1110                1115                1120

Tyr His Gly Thr Lys Gly Glu His Thr Ser Arg Lys Asp Thr Met Thr
                1125                1130                1135

Ala Gln Asn Thr Gly Val Ser Thr Leu Tyr Arg Asn Ser Tyr Gly Ala
            1140                1145                1150

Pro Ala Glu Asp Ile Lys Gln Asn Gln Val Ser Thr Gln Pro Val Pro
            1155                1160                1165

Gln Glu Pro Ser Arg Lys Asp Tyr Glu Thr Tyr Gln Pro Phe Pro Asn
        1170                1175                1180

Ser Thr Arg Asn Tyr Asp Glu Ser Phe Phe Glu Asp Gln Val His His
1185                1190                1195                1200

Arg Pro Pro Ala Ser Glu Tyr Thr Met His Leu Gly Leu Lys Ser Thr
                1205                1210                1215

Gly Asn Tyr Val Asp Phe Tyr Ser Ala Ala Arg Pro Tyr Ser Glu Leu
            1220                1225                1230

Asn Tyr Glu Thr Ser His Tyr Pro Ala Ser Pro Asp Ser Trp Val
            1235                1240                1245
```

PROTEINS RELATED TO NEURONAL REGENERATION AND USES THEREOF

This patent application claims the priority of U.S. provisional patent application No. 60/119,835, filed Feb. 12, 1999 which is incorporated herein by reference.

FIELD OF THE INVENTION

The present invention relates generally to the treatment of neurological injury and dysfunction associated with central nervous system trauma. In particular, the invention is directed to the identification of proteins which induce neuronal regeneration.

BACKGROUND OF THE INVENTION

The peripheral nervous system (PNS) comprises highly organized groups of axon fibers or nerves external to the brain and spinal cord, such as the nerves in the limbs. In response to nerve damage, the peripheral nervous system often attempts to repair itself. While the return of lost functions is usually incomplete, generally the injured organism can adapt and function.

By contrast, damage to the central nervous system (CNS), comprising the brain and spinal cord, is generally more serious, usually causing permanent severe disability or even death.

A number of conditions are known to affect both growth and spontaneous regeneration in nerves, but the underlying mechanisms are not well understood (Gibson et at, In *Compend. Contin. Educ. Pract. Vet.*, vol. 11, pp., 1989, 938–945; and Daniloff et al., J. Cell Bio., 1986, 103:929–945). These conditions include the location of injury, the type of injury, the severity of injury, and the age and general health of the patient.

It has been reported that minor prior recoveries somehow prime the nerve for greater recovery in secondary lesions, for example, recovery from an earlier compression injury.

There are no previous reports of an effective treatment for injuries to neurons of the central nervous system, i.e., the brain and spinal cord (see, M. Walker, New Engl. J. Med., 1991, 324:1885–1887.

The lack of effective treatments for nervous system injuries may be due to an insufficient understanding both of the formation of the nervous system and of its responses to injuries. Several attempts have been made to electrically stimulate injured nerves to try to cause regrowth; recovery was highly variable and inadequate (see, B. Sisken et al., Restorative Neurology and Neuroscience, 1990, 1:303–309; see generally J. Daniloff et al., "The Molecular Bases of Nerve Regeneration," in S. Malhotra (ed.), Advances in Neural Science, vol. 2, 1993). The method that is currently used most often to close gaps in severed nerves uses grafts of the patient's own sensory nerves, typically taken from the ankle; a minimal degree of recovery and permanent analgesia of the donor foot are the usual results.

Because an injured spinal cord has very limited ability to recover spontaneously, and because the consequnces of spinal cord injuries can be so serious, there is a particular need for an effective treatment of spinal cord injuries. Paralytic spinal cord injuries in the United States alone occur at the rate of about 10,000 per year. Although the mortality rate is less than 10%, approximately 720 Americans per million population are permanently disabled as a result of spinal cord injuries. Most of the injured are young people in the most productive stage of life.

Following injury to neuronal cells in the central nervous system, there is often an abortive attempt by injured neural cells to generate new cellular extensions (dendrites and axons) in order to reestablish inter-neural contacts. In the central nervous system, these nerve sprouting and regeneration activities are often modest and only poorly sustained such that regeneration following stroke, trauma, spinal cord injury, etc., does not usually occur.

Thus, there is a need in the art for material and methods for treating neuronal injury.

SUMMARY OF THE INVENTION

The present invention addresses this need. Applicants have surprisingly discovered that a neuron-specific armadillo protein—Neural Plakophilin Related Armadillo Protein (NPRAP)—causes the development of numerous long, cellular extensions, which are similar to axonal sprouting observed during neuronal regeneration and synapse formation.

One aspect of the invention is directed to a method of stimulating growth of nerve cells, which method comprises contacting the nerve cells with an hNPRAP having nerve growth stimulating activity in an amount effective to cause nerve cell growth.

In a specific embodiment related to a method of stimulating growth of nerve cells, the method comprises contacting nerve cells with an hNPRAP stimulating agent in an amount sufficient to induce the expression of an hNPRAP and cause nerve cell growth.

A further related aspect of the invention is directed to a method of stimulating neuronal regeneration in a mammal, which method comprises administering to the mammal in need thereof an effective amount of an hNPRAP or an effective amount of an hNPRAP expression stimulating agent as set forth above.

A further aspect of the invention is related to a pharmaceutical composition comprising an hNPRAP having nerve growth stimulating activity, and a pharmaceutically acceptable carrier.

Yet another aspect of the invention is related to a pharmaceutical composition comprising an hNPRAP expression stimulating agent and a pharmaceutically acceptable carrier.

In a specific embodiment, the invention provides a pharmaceutical composition comprising an hNPRAP gene therapy vector, which vector comprises a polynucleotid encoding hNPRAP and a promoter for expressing hNPRAP, and a carrier. Naturally, such gene therapy vectors are also part of the invention as well.

A further aspect of the invention relates to a method for identifying substances that modulate the expression of hNPRAP, which method comprises contacting cultured cells that express hNPRAP with a test substance measuring levels of hNPRAP, as compared to a control in which the same cells that express hNPRAP are not contacted with the test substance, as an indication of modulatory activity of said test substance.

These and other aspects of the invention are disclosed more fully in the accompanying detailed description.

DETAILED DESCRIPTION

The human Neural Plakophilin Related Annadillo Protein ("hNPRAP") (also described as GT24) consensus cDNA (SEQ ID NO:3) encodes a protein (SEQ ID NO:4) of 1084 amino acid residues with a unique N-terminus, but with homology to proteins with armadillo (arm) repeat motifs at its C-terminus.

Applicants have now discovered that over-expression of hNPRAP, or functional derivatives thereof containing one or more armadillo repeats, causes the development of numerous long, dendritic processes which typically terminate upon distantly located cells. These target cells need not necessarily be expressing hNPRAP. The hNPRAP induced cellular extensions are highly similar to the axonal sprouting seen during neuronal regeneration and synapse formation.

Nucleotides 2920–2997 of the hNPRAP cDNA overlap the anonymous microsatellite locus D5S478, therefore placing the hNPRAP gene on chromosome 5p15 near the Cri-du-Chat deletion locus, a syndrome associated with congenital malformation and gross mental retardation. hNPRAP is described in detail in copending commonly assigned U.S. application Ser. No. 08/888,077, filed Jul. 3, 1997 (PCT/CA97/00051), and Ser. No. 09/227,725, filed Jan. 8, 1999 (PCT/CA99/00018), both of which are incorporated herein by reference.

As described in U.S. application Ser. No. 08/888,077 (PCT/CA97/00051) and Ser. No. 09/227,725 (PCT/CA99/00018), hNPRAP is known to interact with Presenilin I ("PS1") and Presenilin II ("PS2") by direct protein:protein interaction studies. The domain of the PS1 protein that interacts with hNPRAP has also been shown to interact with other proteins, such as armadillo repeat proteins p0071 and β-catenin.

On Northern blots, the hNPRAP gene is expressed as a range of transcripts of 3.9 to 5.0 kb in several regions of adult human brain, but is expressed at only very low levels in most non-neurologic tissues. Studies have shown that PS1 and hNPRAP are both expressed in the same cell types and in adjacent/contiguous subcellular compartments.

In situ hybridization studies indicate that the transcriptional pattern of PS1 and NPRAP overlap both in the brain of 4 month old mice, and in the neural tube and dorsal root ganglia of murine embryos. Both geese are expressed at high levels in dentate and hippocampal neurons, in scattered neocortical neurons, and in cerebellar Purkinje cells in adult mouse brain (Lee et al., J. Neurosci., 1996, 16:7513–7525; Paffenholz and Franke, Differentiation, 1997, 61:293–304). Immunocytochemical studies show that PS1 and hNPRAP have overlapping intracellular distributions. Thus, in non-confluent transfected cell cultures, hNPRAP has a predominantly perinuclear cytoplasmic distribution contiguous with that of PS1. In contrast, in confluent cells with abundant cell:cell contacts, hNPRAP is predominantly located near the cell membrane close to inter-cellular contact zones while PS1 retains its predominantly perinuclear distribution.

The invention is directed to the use of an hNPRAP to stimulate neuronal regeneration and axon sprouting following a wide variety of insults and injuries. An "hNPRAP" is defined herein as a biologically active polypeptide that contains a sequence of hNPRAP that mediate its nerve cell growth stimulating activity, e.g., the armadillo repeats. Thus, hNPRAP includes fill-length (naturally occurring) hNPRAP, as well as biologically active analogues thereof. By "analogues" it is meant modifications such as point mutations, amino acid substitutions, additions or deletions, or other mammalian homologues, such as mouse (SEQ ID NO:5 and SEQ ID NO:6), which have similar activity to hNPRAP, the identification and selection of which are well-known to those skilled in the art. In addition to hNPRAP, the use of recombinant proteins such as p120cas and chimeric proteins having all or parts of the C-terminal armadillo-like repeat and C-terminal unique sequences of hNPRAP may also be utilized in the practice of this invention. Analogues of these proteins which replicate the effects thereof may also be utilized in the practice of this invention.

In a first embodiment, the invention provides a method of stimulating growth of nerve cells, comprising contacting nerve cells with an hNPRAP.

A second embodiment is directed to a method of stimulating growth of nerve cells, comprising contacting nerve cells with an hNPRAP stimulating agent in an amount sufficient to induce the expression of hNPRAP. Such agents may induce the expression of hNPRAP by positively binding to the hNPRAP gene to induce expression, or may alter the interaction of hNPRAP with an inhibitor of hNPRAP expression, e.g., by binding to the inhibitor itself or to hNPRAP such that the inhibitor no longer modulates the expression of hNPRAP.

Alternatively, the expression of hNPRAP may be induced by the use of an appropriate viral vector system, or by the administration of recombinant proteins, biological molecules or small molecules which simulate or resemble either the armadillo binding domain of the presenilins or the armadillo repeats of hNPRAP. Another embodiment is directed to a method for identifying substances that simulate or resemble (mimic) either the armadillo binding domain of the presenilins or the armadillo repeats of hNPRAP, and which substances cause neural growth. Candidate compounds which are shown to mimic either the armadillo binding domain of the presenilins or the armadillo repeats of hNPRAP may be produced in pharmaceutically usefull quantities for use in the treatment of neurological injury and dysfunction associated with central nervous system trauma. Candidate compounds include endogenous cellular components which interact with the presenilins in vivo and which, therefore, provide new targets for pharmaceutical and therapeutic interventions, as well as recombinant, synthetic and otherwise exogenous compounds which may have presenilin binding capacity and, therefore, may be candidates for pharmaceutical agents. Thus, in one procedure, cell lysates or tissue homogenates (e.g., human brain homogenates, lymphocyte lysates) may be screened for proteins or other compounds which bind to one of the normal or mutant presenilins. Alternatively, any of a variety of exogenous compounds, both naturally occurring and/or synthetic (e.g., libraries of small molecules or peptides), may be screened for presenilin binding capacity. In each of these embodiments, an assay is conducted to detect binding between a presenilin component containing at least the interacting domain of a presenilin protein described herein and some other moiety.

As described in U.S. application Ser. No. 09/227,725, the presenilin domain that interacts with PS-interacting proteins, such as armadillo repeat proteins hNPRAP, p0071 and β-catenin, has been identified as including or being contained in the sequence of amino acid residues from about 260 to about 409 of PS1 or corresponding residues from about 260 to about 390 in PS2. More preferably, the inter domain contains or is contained in amino acid residues from about 372 to about 399 of PS1 or corresponding residues from about 350 to about 380 in PS2. The amino acid sequences of wild-type human PS1 and PS2 are shown in SEQ ID NO:1 and SEQ ID NO:2, respectively.

Binding may be detected by indirect functional measures reflecting the functional consequences of the interaction (e.g., changes in intracellular $Ca^{2+}$, $Na^+$, $K^+$, or GTP/GDP ratio, changes in apoptosis or microtubule associated protein phosphorylation, changes in Aβ peptide production or changes in the expression of other downstream genes which can be monitored by differential display, 2D gel electrophoresis, differential hybridization, or SAGE methods) or by direct measures such as immunoprecipitation, the Biomolecular Interaction Assay (BIAcore) or alteration of protein gel electrophoresis. The preferred methods involve variations on the following techniques: (1) direct extraction by affinity chromatography; (2) co-isolation of presenilin components and bound proteins or other compounds by immunoprecipitation; (3) BIAcore analysis; and (4) the yeast two-hybrid systems. Other procedures include methods which detect abnormal processing of PS1, PS2, APP, or proteins reacting with PS1, PS2, or APP (e.g., abnormal phosphorylation, glycosylation, glycation amidation or proteolytic cleavage) alterations in presenilin transcription, translation, and post-translational modification; alterations in the intracellular and extracellular trafficking of presenilin gene products; or abnormal intracellular localization of the presenilins.

The proteins or other compounds identified by these methods may then be assayed for their ability to promote sprouting in axons of neuronal cultures or dendrite formation in non-neurological cells using morphometric analyses which are well-known to those skilled in the art of neuronal regeneration. Alternatively, assays for regeneration following sectioning of the optic nerve, spinal cord, etc. in animals may be performed. Such assays are well-known to those in the field of neuronal regeneration.

The proteins or other compounds identified by these methods may be purified and characterized by any of the standard methods known in the art. Proteins may, for example, be purified and separated using electrophoretic (e.g., SDS-PAGE, 2D PAGE) or chromatographic (e.g., HPLC) techniques and may then be microsequenced. For proteins with a blocked N-terminus, cleavage (e.g., by CNBr and/or trypsin) of the particular binding protein is used to release peptide fragments. Further purification/ characterization by HPLC and microsequencing and/or mass spectrometry by conventional methods provides internal sequence data on such blocked proteins. For non-protein compounds, standard organic chemical analysis techniques (e.g., IR, NMR and mass spectrometry; functional group analysis; X-ray crystallography) may be employed to determine their structure and identity.

These hNPRAPs, and compounds which activate hNPRAP, may be employed in combination with a suitable pharmaceutical, physiologically acceptable carrier. Administration of hNPRAP of this invention can be through the administration of hNPRAP peptides agonists or antagonists synthesized from recombinant conducts of hNPRAP DNA or from peptide chemical synthesis (Woo, et al., Protein Engineering, 1989, 3:29–37) or in the form of gene therapy (Goldspiel et al., Clin. Pharm., 1993, 12:488; Wu and Wu, Biotherapy, 1991, 3:87; Mulligan, Science, 1993, 260:926; Morgan and Anderson, Ann. Rev. Biochem., 1993, 62:191; and, May TIBTECH, 1993, 11:155).

Generally, hNPRPA and/or activate agent(s) are administered as pharmaceutical compositions comprising an effective amount of hNPRAP and/or activating agent(s) in a pharmaceutical carrier. These reagents can be combined for therapeutic use with additional active or inert ingredients, e.g., in conventional pharmaceutically acceptable carriers or diluents, e.g., immunogenic adjuvants, along with physiologically innocuous stabilizers and excipients. A pharmaceutical carrier can be any compatible, non-toxic substance suitable for delivering the compositions of the invention to a patient.

The quantities of reagents necessary for effective therapy will depend upon many different factors, including means of administration, target site, physiological state of the patient, and other medicants administered. Thus, treatment dosages should be titrated to optimize safety and efficacy. Animal testing of effective doses for treatment of particular injuries will provide further predicative indication of human dosage. Various considerations are described, e.g., in Gilman et al. (eds.) (1990) Goodman and Gilman's; The Pharmacological Bases of Therapeutics, 8th Ed., Pergamon Press; and Remington's Pharmaceutical Sciences, 17th ed. (1990), Mack Publishing Co., Easton, Pa. Methods for administration are discussed therein and below, e.g., for intravenous, intraperitoneal, or intramuscular administration, transdermal diffusion, and others. Pharmaceutically acceptable carriers include water, saline, buffers and other compounds described, e.g., in the Merck Index, Merck & Co., Rahway, N.J., and in Remington, supra. Slow release formulations, or a slow release apparatus, may be used for continuous administration.

Dosage ranges for hNPRAP and/or activating agent(s) would ordinarily be expected to be in amounts lower than 1 mM concentrations, typically less than about 10 $\mu$M concentrations, usually less than about 100 nM, preferably less and about 10 pM (picomolar), and most preferably less than about 1 fM (femtomolar), with an appropriate carrier. Generally, treatment is initiated with smaller dosages which are less than the optimun dose of the compound. Thereafter, the dosage is increased by small increments until the optimum effect under the circumstance is reached. Determination of the proper dosage and administration regime for a particular situation is within the skill of the art Polypeptides and other compounds of the present invention which activate or inhibit hNPRAP may be employed alone or in conjunction with other compounds, such as therapeutic compounds. Once identified by the methods described above, the candidate compounds may then be produced in quantities sufficient for pharmaceutical administration or testing (e.g., mg or mg or greater quantities), and formulated in a pharmaceutically acceptable carrier (see, e.g., Remington's, supra).

Pharmaceutically acceptable carriers that may be used in these pharmaceutical compositions include, but are not limited to, ion exchangers, alumina, aluminum stearate, lecithin, serum proteins, such as human serum albunmn, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parentally, by spray inhalation, topically, rectally, nasally, buccally, vaginally or via an implanted reservoir. The term "parenteral" as used herein includes subcutaneous, intravenous, intramuscular, intra-articular, intra-synovial, intramural intathecal, intrahepatic, intralesional and intracranial injection or infusion techniques. Preferably, the compositions are administered orally, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of this invention may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petroleum, white petroleum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petroleum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The methods and compositions of this invention may be used to treat nerve damage caused by a wide variety of diseases or physical traumas. These include, but are not limited to, Alzheimer's disease, Parkinson's disease, amyotrophic lateral sclerosis (ALS), multiple sclerosis, stroke and ischemia associated with stroke, neural paropathy, other neural degenerative diseases, motor neuron diseases, sciatic crush, peripheral neuropathy, particularly neuropathy associated with diabetes, spinal cord injuries and facial nerve crush.

The hNPRAP polynucleotides, polypeptides, agonists and antagonists that are polypeptides may be employed in accordance with the present invention by expression of such polypeptides in treatment modalities often referred to as "gene therapy". Thus, for example, cells from a patient may be engineered with a polynucleotide, such as a DNA or RNA, to encode a polypeptide ex vivo. The engineered cells can then be provided to a patient to be treated with the polypeptide. In this embodiment, cells may be engineered ex vivo, for example, by the use of a retroviral plasmid vector containing RNA encoding a polypeptide of the present invention. Such methods are well-known in the art and their use in the present invention will be apparent from the teachings herein.

Similarly, cells may be engineered in vivo for expression of a polypeptide in vivo by procedures known in the art. For example, a polynucleotide of the invention may be engineered for expression in a replication defective retroviral or viral vector, as discussed above. The retroviral expression construct may then be isolated. A packaging cell is transduced with a retroviral plasmid vector containing RNA encoding a polypeptide of the present invention, such that the packaging cell now produces infectious viral particles containing the gene of interest. These viral particles may be administered to a patient for engineering cells in vivo and expression of the polypeptide in vivo. These and other methods for administering a polypeptide of the present invention should be apparent to those skilled in the art from the teachings of the present invention.

Retroviruses or viruses from which the plasmid vectors hereinabove-mentioned may be derived include, but are not limited to, SimiForest Virus, Lenti-virus, Moloney Murine Leukemia Virus, Spleen Necrosis Virus, Rous Sarcoma Virus, Harvey Sarcoma Virus, Avian Leukosis Virus, Gibbon Ape Leukemia Virus, Human Immunodeficiency Virus, Adenovirus, Myeloproliferative Sarcoma Virus, and Mammary Tumor Virus. In a preferred embodiment, the retroviral plasmid vector is derived from Moloney Murine Leukemia Virus.

Such vectors will include one or more promoters for expressing the polypeptide. Suitable promoters which may be employed include, but are not limited to, the retroviral LTR; the SV40 promoter; and the human cytomegalovirus (CMV) promoter described in Miller et al., Biotechniques, 1989, 7:980–990. Cellular promoters such as eukaryotic cellular promoters including, but not limited to, the histone, RNA polymerase III, and β-actin promoters, can also be used. Additional viral promoters which may be employed include, but are not limited to, adenovirus promoters such as the adenoviral major late promoter, thymidine kinase (TK) promoters such as the Herpes Simplex thymidine kinase promoters; the respiratory syncytial virus (RSV) promoters; and B19 parvovirus promoters. The selection of a suitable promoter will be apparent to those skilled in the art from the teachings contained herein.

The nucleic acid sequence encoding the polypeptide of the present invention may be placed under the control of an inducible promoter. Suitable inducible promoters which may be employed include, but are not limited to, the MMT promoter, the metallothionein promoter; heat shock promoters; the albumin promoter; the ApoAI promoter, human globin promoters; viral thymidine kinase promoters; and human growth hormone promoters. The promoter may also be the native promoter which controls the gene encoding the polypeptide.

The retroviral plasmid vector is employed to transduce packaging cell lines to form producer cell lines. Examples of packaging cells which may be transfected include, but are not limited to, the PE501, PA317, .PSI.-2, .omega.-AM, PA12, T19-14X, VT-19-17-H2, .omega.CRE, .omega.CRIP, GP+E-86, GP+envAm12, and DAN cell lines as described in Miller, A., Human Gene Therapy, 1990, 1:5–14. The vector may be transduced into the packaging cells through any means known in the art. Such means include, but are not limited to, electroporation, the use of liposomes, and CaPO$_4$ precipitation. In one alternative, the retroviral plasmid vector may be encapsulated into a liposome, or coupled to a lipid, and then administered to a host. The producer cell line will generate infectious retroviral vector particles, which include the nucleic acid sequence(s) encoding the polypeptides. Such retroviral vector particles may then be employed to transduce eukaryotic cells, either in vitro or in vivo. The transduced eucaryotic cells will express the nucleic acid sequence(s) encoding the polypeptide. Eukayotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

Each patent, patent application, publication, and procedure disclosed in this application is specifically incorporated by reference in its entirety.

What is claimed is:

1. A method of inducing cellular extensions, which method comprises contacting nerve cells with a human Neural Plakophilin Related Armadillo Protein (hNPRAP) in an amount effective to cause cellular extensions, wherein the hNPRAP comprises an amino acid sequence as set forth in SEQ ID NO:4.

2. The method of claim 1, wherein the cellular extensions terminate upon distantly located cells.

* * * * *